United States Patent
Giles et al.

(10) Patent No.: US 6,440,439 B1
(45) Date of Patent: Aug. 27, 2002

(54) HAIR TREATMENT COMPOSITIONS

(75) Inventors: Colin Christopher David Giles; Frances Ann Ellis; Andrew Malcolm Murray; Matthew Leslie Pearce; Pamela Eileen Red, all of Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/497,014

(22) Filed: Feb. 2, 2000

(30) Foreign Application Priority Data

Feb. 5, 1999 (GB) .............................................. 9902632

(51) Int. Cl.$^7$ .......................... A01N 25/34; A61K 47/00
(52) U.S. Cl. .......................... 424/404; 424/401; 424/65
(58) Field of Search ........................... 424/404, 65, 401

(56) References Cited

FOREIGN PATENT DOCUMENTS

| EP | 0409005 | | 1/1991 |
|---|---|---|---|
| EP | 0458600 | | 11/1991 |
| EP | 0466410 | | 1/1992 |
| EP | 0519727 | | 12/1992 |
| WO | wo9804240 | * | 2/1998 |
| WO | WO 98/04241 | * | 2/1998 |
| WO | 98/16538 | | 4/1998 |
| WO | 98/52531 | | 11/1998 |
| WO | wo9909946 | * | 3/1999 |

OTHER PUBLICATIONS

Hoshowski, M. A. "Conditioning of Hair", Hair and Hair Care, pp. 65–104.*

Mitshubishi–Kagaku Foods Corporation, "Various Applications of Sugar Esters to Foods" and "Product Information: Types of Sugar Esters".*

Search Report under Section 17 Application No. GB 99 02632.0.

Kirk–Othmer "Encyclopedia of Chemical Technology" publish 1980, J. W. Wiley & Sons, Third Edition, vol. 9, pp. 798, 799, 804 and 805.

International Search Report Application No. PCT/EP 00/00758 mailed May 2, 2000.

Koresawa, T.: "The moisturizing agent and the moisturizer which consists of this" AN 131:35630, XP002135746 abstract & JP 11 147,816 A (Kuroda Japan K.K., Japan) 6/99).

Derwent Publication Class B03, AN 1994–338,509—XP 002135746& JP 06 264,049 A (Mitsubishi Kasei Corp) 9/94—abstract.

* cited by examiner

Primary Examiner—Neil S. Levy
Assistant Examiner—R. Dewitty
(74) Attorney, Agent, or Firm—Matthew Boxer

(57) ABSTRACT

Hair treatment compositions are provided which have conditioning benefits and which contain a fatty acid polyester of a polyol selected from cyclic polyols, sugar derivatives and mixtures thereof, in which at least 50% by weight of the total fatty acid moieties of the polyester are C20 or higher unsaturated fatty acid moieties. Specific examples of suitable fatty acid polyesters are sucrose trierucate, sucrose pentaerucate, sucrose tetraerucate, sucrose trirapeate, sucrose tetrarapeate, and sucrose pentarapeate, and mixtures thereof. The compositions are typically in the form of shampoos or conditioners and give surprisingly improved overall conditioning, in particular hair softness.

7 Claims, No Drawings

HAIR TREATMENT COMPOSITIONS

FIELD OF THE INVENTION

This invention relates to hair treatment compositions having conditioning benefits and which contain certain fatty acid polyesters of polyols.

BACKGROUND AND PRIOR ART

Fatty acid polyesters of cyclic polyols and/or sugar derivatives have been described in general as a component of hair conditioning formulations in the following documents:

WO98/04241 discloses that a conditioning system comprising a mixture of polyol carboxylic acid ester and particular nonionic water-soluble polymers is valuable in shampoo compositions for the delivery of improved hair feel and manageability. Cationic cellulose derivative polymer materials may be included in the compositions as optional ingredients.

WO96/37594 discloses a mild, foam producing personal cleansing composition with good skin feel attributes which is based on a combination of an oil dispersing nonionic surfactant and dispersed oil phase which is a mixture of a liquid polyol fatty acid polyester and the second oil component comprising one or more non-polar oils preferably selected from mineral oil, petrolatum, water-insoluble silicones, soya bean oils and mixtures thereof. The use of this mixed oil system is said to deliver improved skin feel.

WO98/04240 describes a shampoo composition containing a particular surfactant base of short chain alkyl sulphate and alkyl ethoxy sulphate in combination with a conditioning system comprising an insoluble oil conditioning agent selected from silicone materials, liquid polyol carboxylic acid esters and mixtures thereof.

JP-A-10/077,215 describes a cosmetic material consisting of saccharide fatty acid ester and one or more siloxanes selected from methyl polysiloxane, methyl phenyl siloxane and methyl polycyclosiloxane. The composition is said to provide good combing and feel after washing when used as a hair rinse or treatment. Exemplified are saccharide fatty acid esters having straight chain saturated fatty acid chains of 18–22 carbon atoms, such as stearic, behenic, 12-hydroxystearic and lanolin fatty acid.

WO98/52528 describes topical emollient compositions for hair or skin which comprise a combination of liquid polyol fatty acid polyester and solid oil. The liquid polyol polyesters employed are preferably sugars or sugar alcohols esterified with one or more fatty acids having from 8 to 22 carbon atoms, preferably from 8 to 18 carbon atoms. In order to provide liquid polyesters of suitable type, it is stated that at least about half of the fatty acid incorporated into the polyester molecule must be unsaturated, and that the especially preferred fatty acids in this context are oleic and linoleic acids, and mixtures thereof.

WO98/52531 refers to occlusive emollient cosmetic formulations for hair or skin including solid polyol fatty acid polyesters and liquid oils. The solid polyol fatty acid polyester is typically a sugar polyester and contains a mixture of saturated and unsaturated fatty acid chains. At least 15%, most preferably at least 60% by weight of the total fatty acid moieties of the polyesters are C20 or higher saturated fatty acid moieties.

The present inventors have found that certain selected fatty acid polyesters of cyclic polyols and/or sugar derivatives give surprisingly improved overall conditioning when incorporated into a hair treatment composition.

Furthermore, hair softness is particularly improved.

The compositions of the invention also have particular utility in the treatment of hair which has been damaged, e.g. through environmental exposure or harsh mechanical or chemical treatments such as heat styling, perming or bleaching. In such cases, the benefits of softness and ease of combing provided by compositions of the present invention are especially apparent.

SUMMARY OF THE INVENTION

The present invention provides a hair treatment composition comprising a fatty acid polyester of a polyol selected from cyclic polyols, sugar derivatives and mixtures thereof, in which at least 50% by weight of the total fatty acid moieties of the polyester are C20 or higher unsaturated fatty acid moieties.

DETAILED DESCRIPTION AND PREFERRED EMBODIMENTS (i) Fatty Acid Polyester

An essential component in hair treatment compositions of the invention is a fatty acid polyester of a polyol selected from cyclic polyols, sugar derivatives and mixtures thereof, in which at least 50% by weight of the total fatty acid moieties of the polyester are C20 or higher unsaturated fatty acid moieties.

By "polyol" is meant a material having at least four hydroxyl groups. The polyols used to prepare the fatty acid polyester will preferably have from 4 to 12, more preferably from 4 to 11, most preferably from 4 to 8 hydroxyl groups.

By "fatty acid polyester" is meant a material in which at least two of the ester groups are independently of one another attached to a fatty ($C_8$ to $C_{22}$ alkyl or alkenyl) chain. For a given material, prefixes such as "tetra-", "penta-" indicate the average degrees of esterification. The compounds exist as a mixture of materials ranging from the monoester to the fully esterified ester.

Cyclic polyols are the preferred polyols used to prepare the fatty acid polyester in the present invention. Examples include inositol, and all forms of saccharides. Saccharides, in particular monosaccharides and disaccharides, are especially preferred.

Examples of monosaccharides include xylose, arabinose, galactose, fructose, sorbose and glucose. Glucose is especially preferred.

Examples of disaccharides include maltose, lactose, cellobiose and sucrose. Sucrose is especially preferred.

Examples of suitable sugar derivatives include sugar alcohols, such as xylitol, erythritol, maltitol and sorbitol, and sugar ethers such as sorbitan.

At least 50% by weight of the total fatty acid moieties of the polyesters are C20 or higher unsaturated fatty acid moieties. Preferably, at least 60% by weight of the total fatty acid moieties of the polyesters are C20 or higher unsaturated fatty acid moieties.

Examples of suitable C20 or higher unsaturated fatty acid moieties include erucate, brassidate, nervonate, arachidonate, eicosapentaenoate, eicosenate, eicosadienate, eicosatrienate, docosadienoate, docosatrienoate, docosatetraenoate and docosahexaenoate. For oxidative stability, the mono- and diunsaturated fatty acid moieties are preferred.

Erucate is particularly preferred.

Mixed fatty acid moieties from source oils which contain substantial amounts of the desired unsaturated acids can be used as the acid moieties to prepare fatty acid polyesters suitable for use in the hair treatment composition of the invention. The mixed fatty acids from the oils should contain at least 50%, most preferably at least 60% of the desired unsaturated acids. For example, high erucic rapeseed oil fatty acids can be used instead of pure C20–C22 unsaturated acids. Preferably the C20 and higher acids, or their derivatives, e.g. methyl or other lower alkyl esters, are concentrated, for example by distillation.

Specific examples of suitable fatty acid polyesters are sucrose trierucate, sucrose pentaerucate, sucrose tetraerucate, sucrose trirapeate, sucrose tetrarapeate, and sucrose pentarapeate, and mixtures thereof.

Sucrose pentaerucate and sucrose tetraerucate are particularly preferred. These materials are available commercially as Ryoto Sugar Esters ex Mitsubishi Kasei Foods.

The fatty acid polyester can be prepared by a variety of methods well known to those skilled in the art. These methods include acylation of the cyclic polyol or reduced saccharide with an acid chloride; trans-esterification of the cyclic polyol or reduced saccharide fatty acid esters using a variety of catalysts; acylation of the cyclic polyol or reduced saccharide with an acid anhydride and acylation of the cyclic polyol or reduced saccharide with a fatty acid. Typical preparations of these materials are disclosed in U.S. Pat. No. 4,386,213 and AU 14416/88.

The total amount of fatty acid polyester in hair treatment compositions of the invention is generally from 0.001 to 10% by weight, preferably from 0.01 to 5%, more preferably from 0.01% to 3% by weight of the total hair treatment composition.

(ii) Product Form

Hair treatment compositions according to the invention may suitably take the form of shampoos, conditioners, sprays, mousses or lotions. Preferred hair treatment composition forms are shampoos and conditioners.

Shampoo Compositions

A particularly preferred hair treatment composition in accordance with the invention is a shampoo composition.

Cleansing Surfactant

Such a shampoo composition will comprise one or more cleansing surfactants which are cosmetically acceptable and suitable for topical application to the hair. Further surfactants may be present as an additional ingredient if sufficient for cleansing purposes is not provided as emulsifying agent for oily or hydrophobic components (such as silicones) which may typically be present in the shampoo.

It is preferred that shampoo compositions of the invention comprise at least one further surfactant (in addition to that used as emulsifying agent) to provide a cleansing benefit.

Suitable cleansing surfactants, which may be used singularly or in combination, are selected from anionic, amphoteric and zwitterionic surfactants, cationic surfactants, and mixtures thereof. The cleansing surfactant may be the same surfactant as the emulsifier, or may be different. Preferred cleansing surfactants are selected from anionic, amphoteric and zwitterionic surfactants, and mixtures thereof.

Examples of anionic surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic surfactants for use in shampoos of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

The shampoo composition can also include co-surfactants, to help impart aesthetic, physical or cleansing properties to the composition. A preferred example is a nonionic surfactant, which can be included in an amount ranging from 0% to about 5% by weight based on total weight.

For example, representative nonionic surfactants that can be included in shampoo compositions of the invention include condensation products of aliphatic ($C_8$–$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{—}(G)_n$$

wherein R is a branched or straight chain alkyl group which may be saturated or unsaturated and G is a saccharide group.

R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

The total amount of surfactant (including any co-surfactant, and/or any emulsifying agent) in shampoo compositions of the invention is generally from 0.1 to 50% by weight, preferably from 5 to 30%, more preferably from 10% to 25% by weight of the total shampoo composition.

Cationic Polymer

A cationic polymer is a preferred ingredient in shampoo compositions of the invention, for enhancing conditioning performance of the shampoo. Typically such a polymer enhances deposition of conditioning components such as silicone from the shampoo composition onto the intended site during use, i.e. the hair and/or the scalp.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic polymers can comprise mixtures of monomer units derived from amine- and/or quaternary ammonium-substituted monomer and/or compatible spacer monomers.

Suitable cationic polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and co-polymers of unsaturated carboxylic acids having from 3 to 5 carbon atoms, (as described in U.S. Pat. No. 4,009,256);

cationic polyacrylamides(as described in WO95/22311).

Other cationic polymers that can be used include cationic polysaccharide polymers, such as cationic cellulose derivatives, cationic starch derivatives, and-cationic guar gum derivatives.

Cationic polysaccharide polymers suitable for use in compositions of the invention include those of the formula:

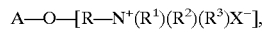

$$A\text{—}O\text{—}[R\text{—}N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (Commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic polymer is selected from cationic cellulose and cationic guar derivatives. Particularly preferred cationic polymers are JAGUAR C13S, JAGUAR C15, JAGUAR C17 and JAGUAR C16 and JAGUAR C162.

Conditioners

Compositions in accordance with the invention may also be formulated as conditioners for the treatment of hair (typically after shampooing) and subsequent rinsing.

Conditioning Surfactant

Such a conditioner will comprise one or more conditioning surfactants which are cosmetically acceptable and suitable for topical application to the hair.

Suitable conditioning surfactants are selected from cationic surfactants, used singly or in admixture. Examples include quaternary ammonium hydroxides or salts thereof, e.g. chlorides.

Suitable cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as DEHYQUART, ex Henkel.

In conditioners of the invention, the level of cationic surfactant is preferably from 0.01 to 10%, more preferably 0.05 to 5%, most preferably 0.1 to 2% by weight of the composition.

Fatty Alcohol

Conditioners of the invention advantageously incorporate a fatty alcohol material. The combined use of fatty alcohol materials and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol material in conditioners of the invention is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

Silicone

Silicone is a particularly preferred ingredient in hair treatment compositions of the invention. In particular, hair shampoos and conditioners of the invention will preferably also comprise emulsified particles of silicone, for enhancing conditioning performance. The silicone is insoluble in the aqueous matrix of the composition and so is present in an emulsified form, with the silicone present as dispersed particles.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO96/31188. These materials can impart body, volume and stylability to hair, as well as good wet and dry conditioning.

The viscosity of the emulsified silicone itself (not the emulsion or the final hair conditioning composition) is typically at least 10,000 cst. In general we have found that conditioning performance increases with increased viscosity. Accordingly, the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in hair shampoos and conditioners of the invention will typically have an average silicone particle size in the composition of less than 30, preferably less than 20, more preferably less than 10 microns. We have found that reducing the particle size generally improves conditioning performance. Most preferably the average silicone particle size of the emulsified silicone in the composition is less than 2 microns, ideally it ranges from 0.01 to 1 micron. Silicone emulsions having an average silicone particle size of $\leq 0.15$ microns are generally termed microemulsions.

Particle size may be measured by means of a laser light scattering technique, using a 2600D Particle Sizer from Malvern Instruments.

Suitable silicone emulsions for use in the invention are also commercially available in a pre-emulsified form.

Examples of suitable pre-formed emulsions include emulsions DC2-1766, DC2-1784, and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

A further preferred class of silicones for inclusion in shampoos and conditioners of the invention are amino functional silicones. By "amino functional silicone" is meant a silicone containing at least one primary, secondary or tertiary amine group, or a quaternary ammonium group.

Examples of suitable amino functional silicones include:

(i) polysiloxanes having the CTFA designation "amodimethicone", and the general formula:

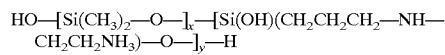

in which x and y are numbers depending on the molecular weight of the polymer, generally such that the molecular weight is between about 5,000 and 500,000.

(ii) polysiloxanes having the general formula:

in which:

G is selected from H, phenyl, OH or $C_{1-8}$ alkyl, e.g. methyl;

a is 0 or an integer from 1 to 3, preferably 0;

b is 0 or 1, preferably 1;

m and n are numbers such that (m+n) can range from 1 to 2000, preferably from 50 to 150;

m is a number from 1 to 2000, preferably from 1 to 10;

n is a number from 0 to 1999, preferably from 49 to 149, and

R' is a monovalent radical of formula —$C_qH_{2q}L$ in which q is a number from 2 to 8 and L is an aminofunctional group selected from the following:

—NR"—CH$_2$—CH$_2$—N(R")$_2$

—N(R")$_2$

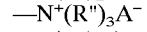

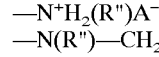

in which R" is selected from H, phenyl, benzyl, or a saturated monovalent hydrocarbon radical, e.g. $C_{1-20}$ alkyl, and;

A is a halide ion, e.g. chloride or bromide.

Suitable amino functional silicones corresponding to the above formula include those polysiloxanes termed "trimethylsilylamodimethicone" as depicted below, and which are sufficiently water insoluble so as to be useful in compositions of the invention:

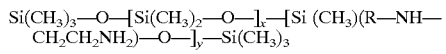
Si(CH$_3$)$_3$—O—[Si(CH$_3$)$_2$—O—]$_x$—[Si (CH$_3$)(R—NH—CH$_2$CH$_2$NH$_2$)—O—]$_y$—Si(CH$_3$)$_3$ wherein x+y is a number from about 50 to about 500, and wherein R is an alkylene group having from 2 to 5 carbon atoms. Preferably, the number x+y is in the range of from about 100 to about 300.

(iii) quaternary silicone polymers having the general formula:

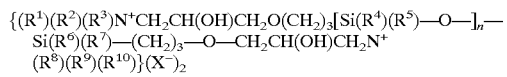
{(R$^1$)(R$^2$)(R$^3$)N$^+$CH$_2$CH(OH)CH$_2$O(CH$_2$)$_3$[Si(R$^4$)(R$^5$)—O—]$_n$—Si(R$^6$)(R$^7$)—(CH$_2$)$_3$—O—CH$_2$CH(OH)CH$_2$N$^+$(R$^8$)(R$^9$)(R$^{10}$)}(X$^-$)$_2$ wherein R$^1$ and R$^{10}$ may be the same or different and may be independently selected from H, saturated or unsaturated long or short chain alk(en)yl, branched chain alk(en)yl and C$_5$–C$_8$ cyclic ring systems;

R$^2$ thru' R$^9$ may be the same or different and may be independently selected from H, straight or branched chain lower alk(en)yl, and C$_5$–C$_8$ cyclic ring systems;

n is a number within the range of about 60 to about 120, preferably about 80, and X$^-$ is preferably acetate, but may instead be for example halide, organic carboxylate, organic sulphonate or the like. Suitable quaternary silicone polymers of this class are described in EP-A-0 530 974.

Amino functional silicones suitable for use in shampoos and conditioners of the invention will typically have a mole % amine functionality in the range of from about 0.1 to about 8.0 mole %, preferably from about 0.1 to about 5.0 mole % most preferably from about 0.1 to about 2.0 mole %. In general the amine concentration should not exceed about 8.0 mole % since we have found that too high an amine concentration can be detrimental to total silicone deposition and therefore conditioning performance.

The viscosity of the amino functional silicone is not particularly critical and can suitably range from about 100 to about 500,000 cst.

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Also suitable are emulsions of amino functional silicone oils with non ionic and/or cationic surfactant.

Suitably such pre-formed emulsions will have an average amino functional silicone particle size in the shampoo composition of less than 30, preferably less than 20, more preferably less than 10 microns. Again, we have found that reducing the particle size generally improves conditioning performance. Most preferably the average amino functional silicone particle size in the composition is less than 2 microns, ideally it ranges from 0.01 to 1 micron. Silicone emulsions having an average silicone particle size of ≦0.15 microns are generally termed microemulsions.

Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

An example of a quaternary silicone polymer useful in the present invention is the material K3474, ex Goldschmidt.

The total amount of silicone incorporated into compositions of the invention depends on the level of conditioning desired and the material used. A preferred amount is from 0.01 to about 10% by weight of the total composition although these limits are not absolute. The lower limit is determined by the minimum level to achieve conditioning and the upper limit by the maximum level to avoid making the hair and/or skin unacceptably greasy.

We have found that a total amount of silicone of from 0.3 to 5%, preferably 0.5 to 3%, by weight of the total composition is a suitable level.

Optional Ingredients

Compositions of this invention may contain any other ingredient normally used in hair treatment formulations. These other ingredients may include viscosity modifiers, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts.

(ii) hair fibre benefit agents. Examples are:

ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

free fatty acids, for cuticle repair and damage prevention. Examples are branched chain fatty acids such as 18-methyleicosanoic acid and other homologues of this series, straight chain fatty acids such as stearic, myristic and palmitic acids, and unsaturated fatty acids such as oleic acid, linoleic acid, linolenic acid and arachidonic acid. A preferred fatty acid is oleic acid. The fatty acids may be added singly, as mixtures, or in the form of blends derived from extracts of, e.g. lanolin.

Mixtures of any of the above active ingredients may also be used.

The invention is further illustrated by way of the following non-limitative Examples, in which all percentages quoted are by weight based on total weight unless otherwise stated.

EXAMPLES

Example 1

Comparative Tests of Wet and Dry Conditioning Properties

Five sugar polyesters were investigated in solution for their conditioning effect on wet and dry properties of hair treated with the solutions as described in the following Table:

| Sample | Sugar Polyester | Concentration in dichloromethane |
|---|---|---|
| A | sucrose pentalaurate (C12 saturated) | 0.5 |
| B | sucrose pentatallowate (C16–C18 saturated) | 0.5 |
| C | sucrose pentastearate (C18 saturated) | 0.5 |
| D | sucrose pentaoleate (C18 monounsaturated) | 0.5 |
| E | sucrose pentaerucate (C22 monounsaturated) | 0.5 |

Methodology

Before using hair switches any residues on the hair were removed by 'ethering' them. 7 g, 10 inch Spanish hair switches were soaked in ether for 15 minutes and then dipped in a 5% sodium lauryl ether sulphate solution and left in a fume cupboard until all traces of ether had evaporated. The switches were rinsed in warm running water until the water ran clear.

100 ml solutions of each sugar polyester were prepared (0.5% in dichloromethane) and the ethered hair switch was immersed in the solution for 5 minutes. The switch was taken out, drained and allowed to dry in the fume cupboard. Duplicates were prepared for each test product.

Each test product is scored alongside two standard switches, one of which is not conditioned and is ranked as 1 and one that is highly conditioned and ranked as 9. The test switches are scored by the panellist by comparison with switches 1 and 9 for smoothness, ease of comb, greasiness and lack of flyaway in both wet and dry states.

The standard switches ranked 1 and 9 were hung from a panel stand and the panellist was asked to evaluate them for smoothness, ease of comb, greasiness and lack of flyaway. Once they were aware of the standard conditions for poor (1) and good (9), they were presented with test switches one at a time and asked to score them for each attribute. The switches were presented to the panellists in a random order, 20 panellists were used for each test. The test was completed first in the dry state and then later, after spraying with tap water, in the wet state. The results were analysed by analysis of variance.

The results were as shown in the following Table:

| Sample | Smooth feel wet | Ease of comb wet | Smooth feel dry | Ease of comb dry | Lack of flyaway |
|---|---|---|---|---|---|
| A | 5.49 | 3.44 | 5.75 | 6.90 | 6.99 |
| B | 4.48 | 3.50 | 5.75 | 6.70 | 6.65 |
| C | 3.15 | 0.84 | 5.30 | 5.98 | 7.20 |
| D | 5.11 | 2.43 | 5.73 | 5.80 | 7.80 |
| E | 6.60 | 5.25 | 6.83 | 8.50 | 6.05 |

The scores represent the average panellist score for each attribute.

The results show that hair switches treated with sample E (according to the invention) show appreciably improved conditioning assessed over a variety of wet and dry conditioning attributes, as compared with hair switches treated with samples A to D (comparative examples). Surprisingly, it is apparent from the above testing that increasing the chain length of a saturated fatty acid moiety reduces the conditioning effect, whereas for an unsaturated fatty acid moiety, the opposite is observed (conditioning effect increases with increasing chain length).

Example 2

A shampoo composition was prepared by mixing the following components in the amounts stated.

| Component | % by weight |
|---|---|
| Sodium lauryl ether sulphate 2EO | 14.0 |
| Cocamidopropyl betaine | 2.0 |
| Jaguar C13S | 0.2 |
| CARBOPOL ETD 2020 | 0.4 |
| Silicone emulsion[1] | 1.5 |
| EUPERLAN PK3000[2] | 6.0 |
| Sucrose tetraerucate[3] | 0.025 |
| Preservative, colour, fragrance | q.s. |
| Water, minors | to 100% |

[1] Added as DC2-1766 (emulsion of dimethiconol in anionic surfactant, 60% active, ex Dow Corning)
[2] Glycol stearate pearlizer, (ex Henkel)
[3] Added as Ryoto Sugar Ester ER290 (ex Mitsubishi Kasei Foods).

What is claimed is:

1. A hair treatment composition comprising a fatty acid polyester of a polyol selected from cyclic polyols, sugar derivatives and mixtures thereof, in which at least 50% by weight of the total fatty acid moieties of the polyester are C20 or higher unsaturated fatty acid moieties.

2. A hair treatment composition according to claim 1, in which at least 60% by weight of the total fatty acid moieties of the polyester are C20 or higher unsaturated fatty acid moieties.

3. A hair treatment composition according to claim 1 or claim 2, in which the polyol used to prepare the fatty acid polyester is a saccharide.

4. A hair treatment composition according claim 1, in which the C20 or higher unsaturated fatty acid moieties are selected from the group consisting of erucate, brassidate, nervonate, arachidonate, eicosapentaenoate, eicosenate, eicosadienate, eicosatrienate, docosadienoate, docosatrienoate, docosatetraenoate and docosahexaenoate, and mixtures thereof.

5. A hair treatment composition according to claim 1, in which the fatty acid polyester is selected from the group consisting of sucrose trirapeate, sucrose tetrarapeate, sucrose pentarapeate, sucrose trierucate, sucrose pentaerucate and sucrose tetraerucate, and mixtures thereof.

6. A hair treatment composition according to any preceding claim which is in the form of a shampoo composition and which further comprises one or more cleansing surfactants, a cationic polymer and emulsified particles of silicone.

7. A hair treatment composition according to any of claims 1 to 5 which is in the form of a conditioner and which further comprises one or more conditioning surfactants, a fatty alcohol and emulsified particles of silicone.

* * * * *